(12) United States Patent
Biedermann et al.

(10) Patent No.: US 6,723,100 B2
(45) Date of Patent: Apr. 20, 2004

(54) BONE SCREW AND FASTENING TOOL FOR SAME

(75) Inventors: Lutz Biedermann, Villingen (DE); Jürgen Harms, Karlsruhe (DE)

(73) Assignee: Biedermann Motech GmbH, Schwenningen (DE)

( * ) Notice: Subject to any disclaimer, the term of this patent is extended or adjusted under 35 U.S.C. 154(b) by 0 days.

(21) Appl. No.: 10/198,603

(22) Filed: Jul. 17, 2002

(65) Prior Publication Data

US 2003/0023243 A1 Jan. 30, 2003

(30) Foreign Application Priority Data

Jul. 27, 2001 (DE) .......................... 101 36 129

(51) Int. Cl.[7] .............................................. A61B 17/56
(52) U.S. Cl. ............................................ 606/73; 606/61
(58) Field of Search ............................. 606/61, 72, 73

(56) References Cited

U.S. PATENT DOCUMENTS

| | | | | |
|---|---|---|---|---|
| 5,716,356 A | * | 2/1998 | Biedermann et al. | 606/61 |
| 5,725,527 A | * | 3/1998 | Biedermann et al. | 606/61 |
| 2002/0058942 A1 | * | 5/2002 | Biedermann et al. | 606/73 |
| 2002/0143341 A1 | * | 10/2002 | Biedermann et al. | 606/73 |
| 2003/0100904 A1 | * | 5/2003 | Biedermann et al. | 606/73 |
| 2003/0125741 A1 | * | 7/2003 | Biedermann et al. | 606/61 |

FOREIGN PATENT DOCUMENTS

| | | |
|---|---|---|
| EP | 0 483 242 B1 | 5/1992 |
| EP | 0 614 649 A1 | 9/1994 |

* cited by examiner

*Primary Examiner*—Pedro Philogene
*Assistant Examiner*—D. Austin Bonderer
(74) *Attorney, Agent, or Firm*—George W. Neuner; Edwards & Angell, LLP

(57) ABSTRACT

The invention relates to a bone screw and a tool for fixing same. A bone screw has a screw element (1), comprising a screw shank (2) and a screw head (3), a cylindrical receiver part (5) with a bore coaxial to the cylindrical axis coming from one end (8) of the cylinder, an opening (6) extending cross-wise to the cylindrical axis for receiving a rod (16) to be connected to the bone screw, an inner thread (10) at one end (8) and a screw (13) cooperating with it and also an outer thread (11) at one end (8) and a nut (14) cooperating with it. Both threads (10, 11) are constructed as running in opposite directions. A fastening tool (21, 21') acts as tool for fixing a bone screw, with a central shank (23), which is constructed at one end for engagement with a screw or nut and at its other end has a first handle (22), a sleeve-shaped shank (24), surrounding the central shank (23), which is constructed at one end for engagement with a screw or nut and at its other end has a second handle (25), both shanks (23, 24) being rotatable with respect to one another.

7 Claims, 4 Drawing Sheets

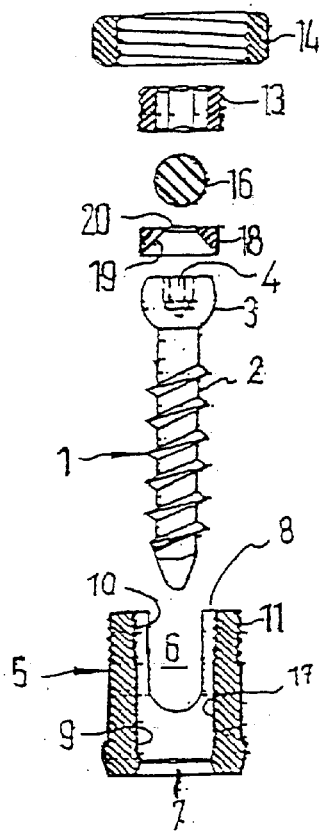
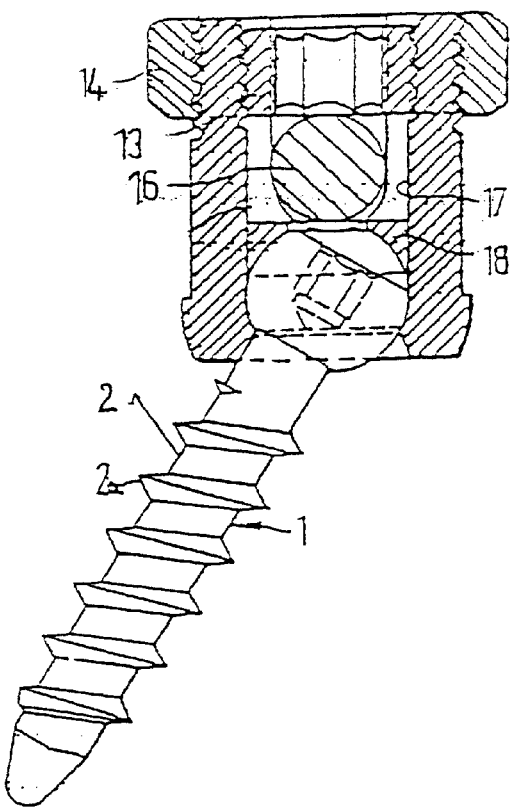
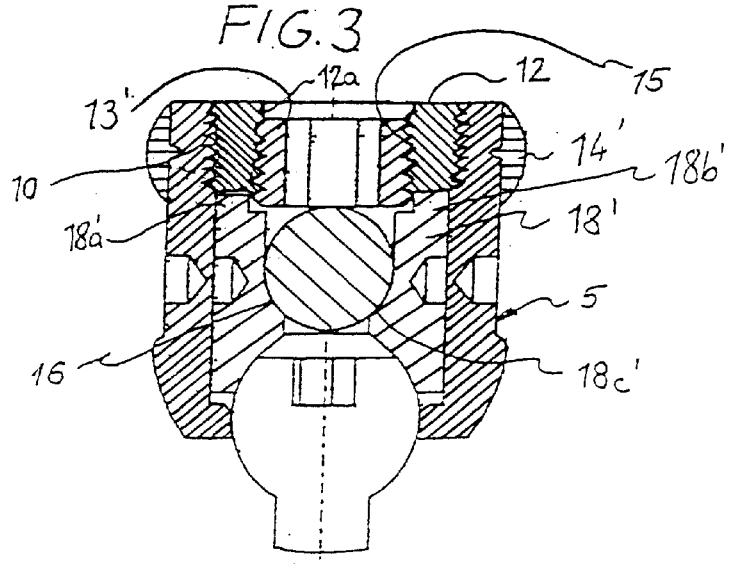

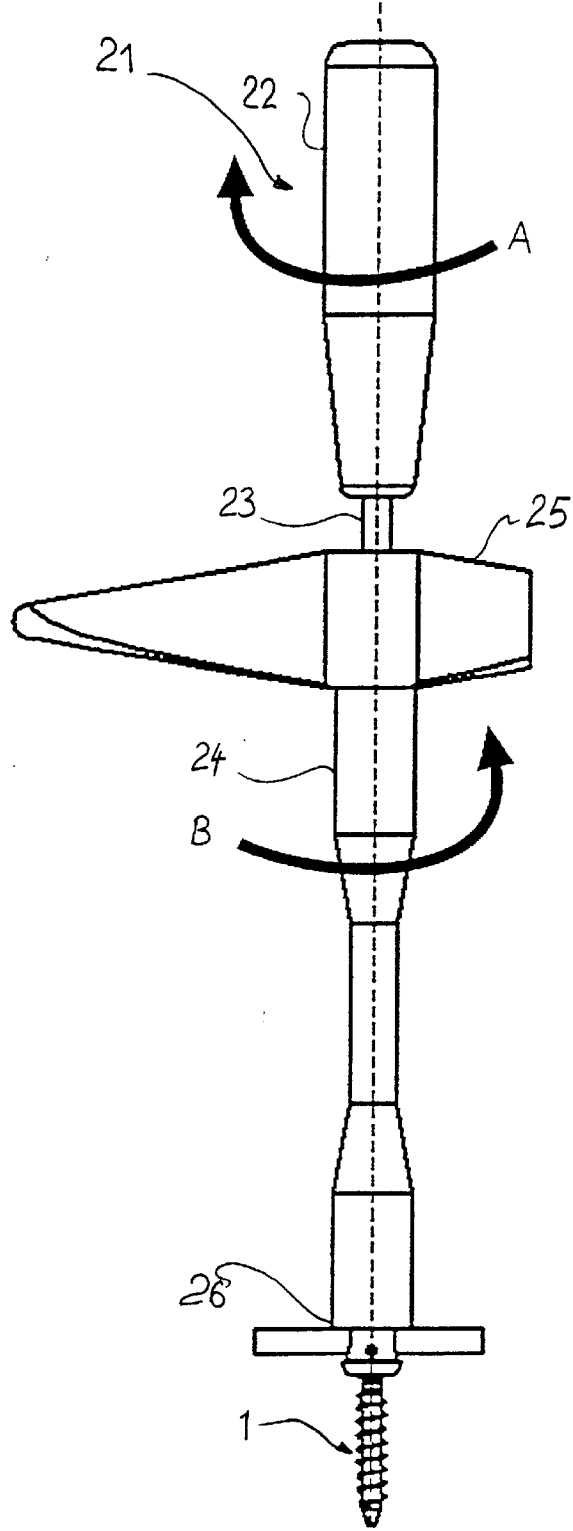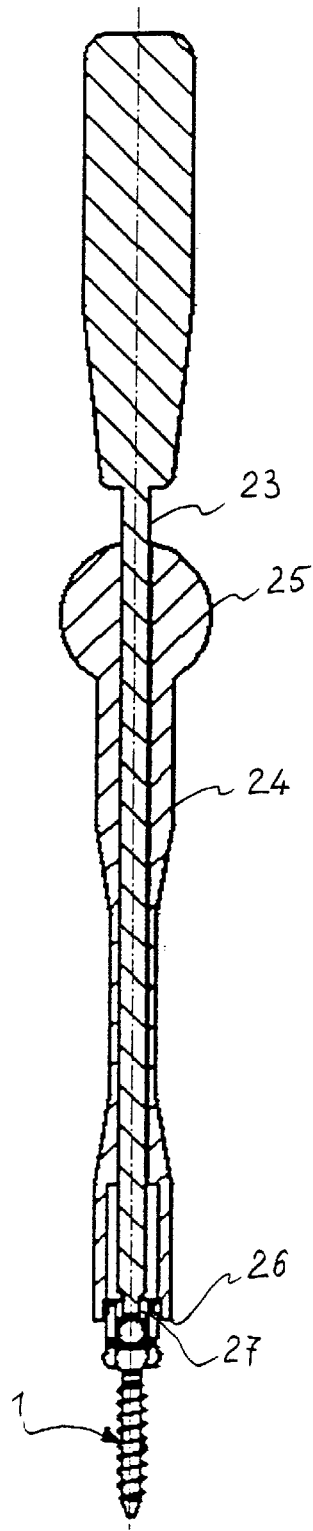

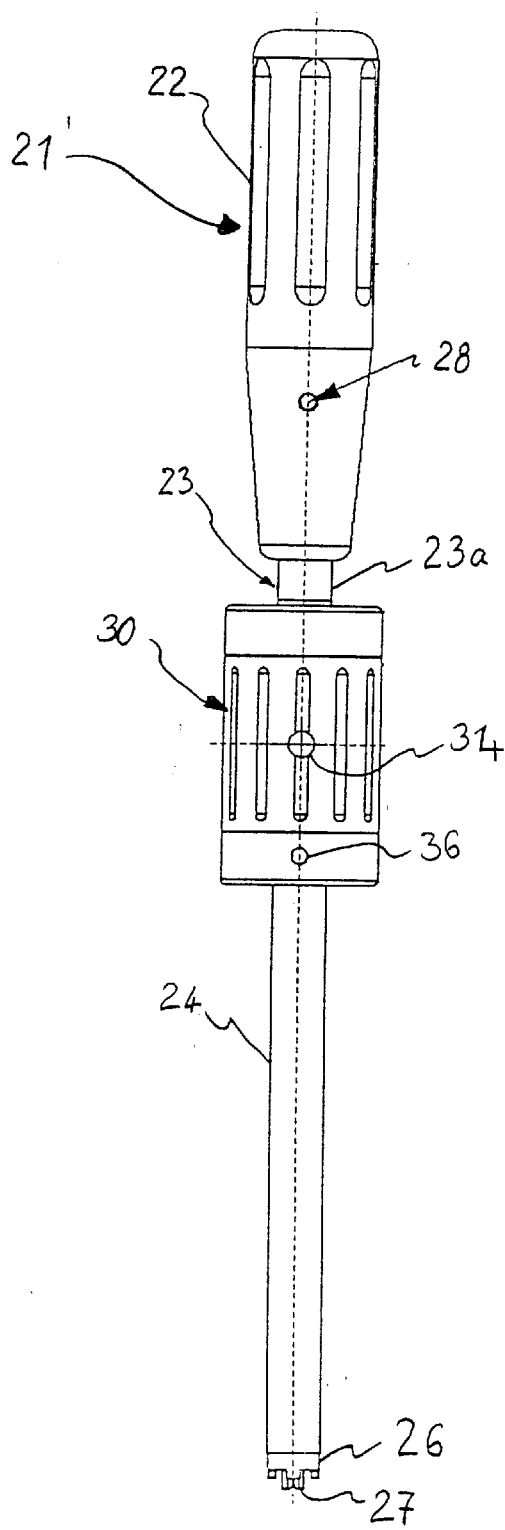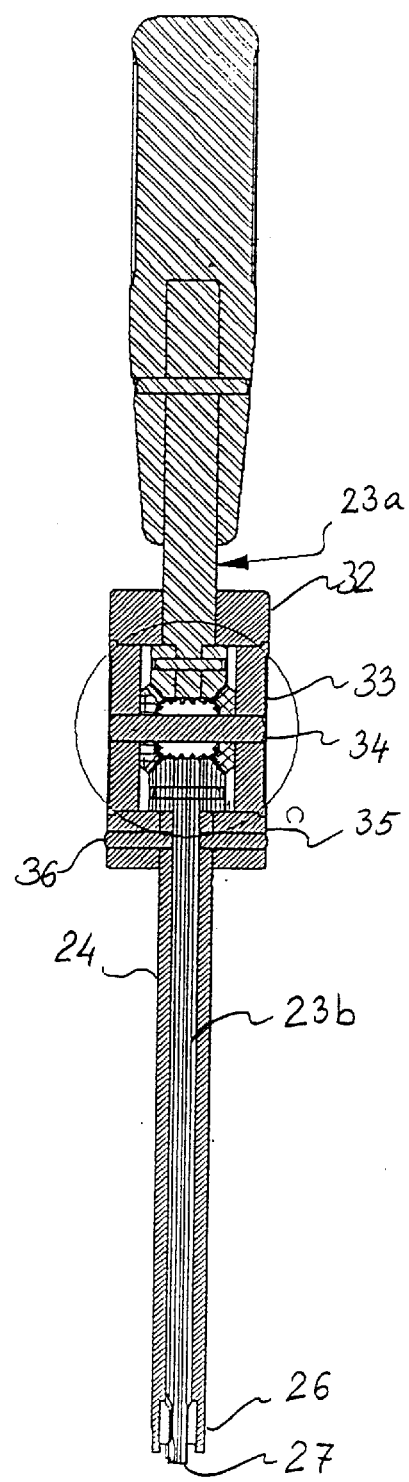

BONE SCREW AND FASTENING TOOL FOR SAME

The invention relates to a bone screw and an associated fastening tool for fixing the bone screw.

A bone screw is known, for example, from EP 0 483 242 B1. A bone screw is known from EP 0 614 649 A1. With these bone screws high torques are applied when the screws are driven home and also for fixing the screw element and for fixing the rod. As the screws have to be finally tightened during the operation by the person performing the operation—after inserting the rod—there is a danger of damaging the vertebra concerned. If the screws are not sufficiently finally tightened, there is a danger that the screws/rod connections will come loose and the bone screw will lose its fixed position.

It is the object of the invention to improve the way of fixing the bone screw, in order on the one hand to be able to apply sufficiently high torques for permanent fixing of the screws and on the other hand to reduce or avoid transfer of support moments on to the bone or the vertebra during screwing down.

By means of the screw connection in opposite directions both screw elements can be fixed at the same time. The respective support moment which occurs on tightening a screw element therein simultaneously serves as a torque supporting the screw connection of the other screw element. In this way higher torques can be applied without a dangerous torque being introduced into the bone of the patient.

With the tool according to the invention it is possible to apply a high torque in two opposite directions, so they almost cancel one another out. It is further possible for the user to vary the torque individually for the two screw elements in a simple way.

Further advantageous configurations of the invention are the subject of the subordinate claims.

In the following description of preferred embodiments the invention is explained with reference to the figures.

FIG. 1 shows an exploded illustration of a first embodiment of a bone screw according to the invention, illustrated partially in section.

FIG. 2 shows an illustration partially in section of the first embodiment in the assembled state.

FIG. 3 shows an alternative embodiment of a bone screw illustrated as enlarged and partially in section.

FIG. 4 shows the side view of a first embodiment of a fastening tool.

FIG. 5 shows the side view of the fastening tool from FIG. 4 illustrated in section.

FIG. 6 shows the side view of a second embodiment of a fastening tool.

FIG. 7 shows the side view of the fastening tool from FIG. 6 illustrated in section.

FIRST EMBODIMENT

Figure 8:
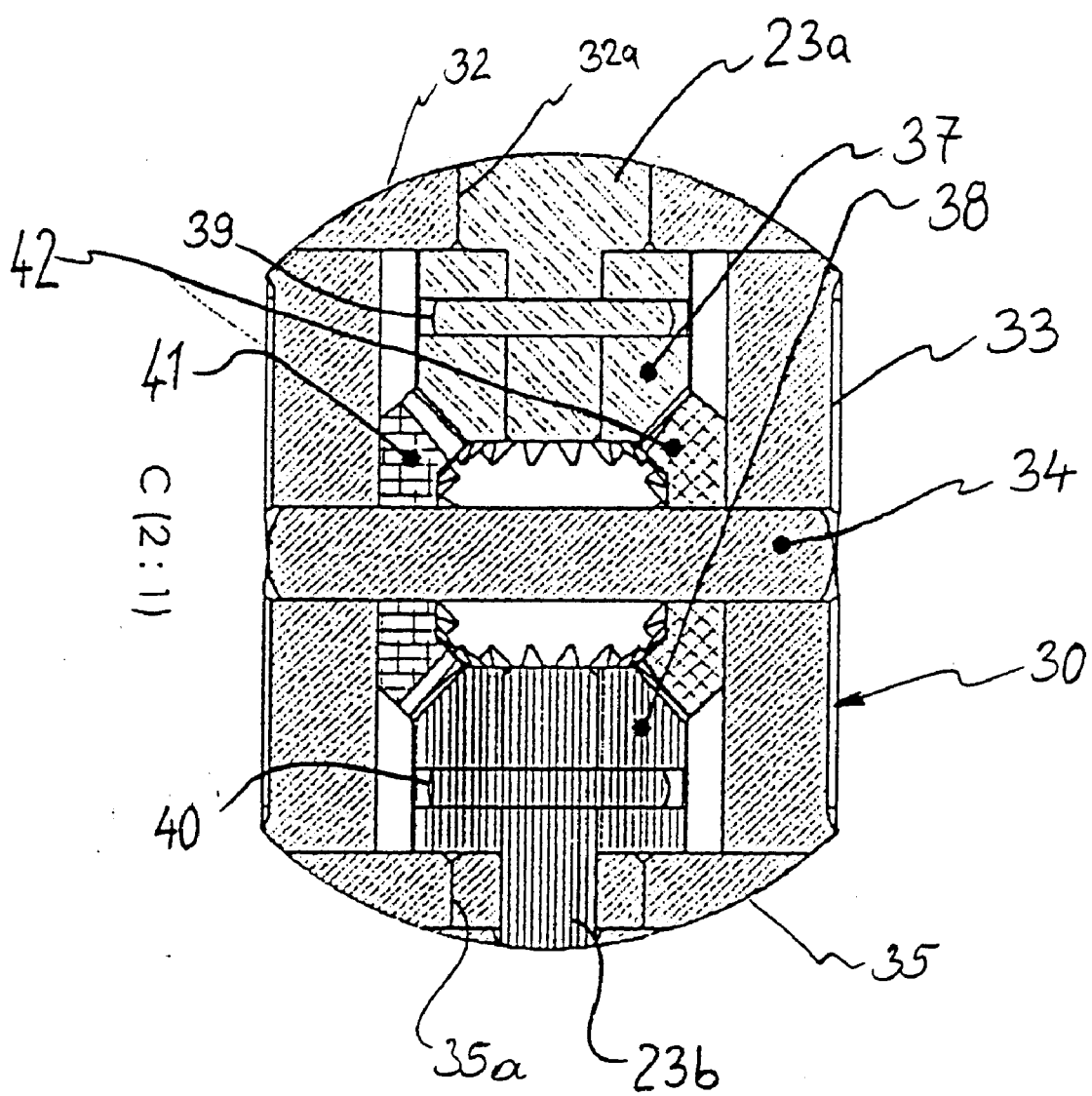
FIG. 8 shows a detail C from FIG. 7 in enlarged illustration.

FIG. 2 shows a bone screw in assembled state. It has an actual screw element 1 with a screw shank 2 with a thread section 2a and a head 3. The head is constructed as a segment of a sphere. Coaxially to the thread axis and on the end opposite the thread section 2a the head 3 has a recess 4 for bringing into engagement with a box spanner. The recess 4 can also have another suitable shape, however.

The bone screw further comprises a cylindrically constructed receiver part 5. This has at one end a first bore 7, aligned symmetrically to the axis, the diameter of which is larger than that of the thread section 2a and smaller than that of the head 3. The receiver part 5 further has a coaxial second bore 8, which is open at the end opposite the first bore 7 and the diameter of which is large enough for the screw element to be guided through the open end with its thread section through the first bore 7 and with its head 3 to the floor of the second bore 8. Between the first and the second bore a small coaxial section 9 is provided, which is immediately adjacent to the first bore 7 and is constructed as spherical towards the open end, wherein the radius is substantially equal to the radius of the section of the head 3 shaped as the segment of a sphere. Adjacent to the section 9 the second bore 8 has a cylindrical section 17, to which an inner thread 10, extending to the open end, adjoins. The inner thread 10 is constructed in the present embodiment as a right-hand thread.

The receiver part 5 further has an opening in the form of a U-shaped recess 6, arranged symmetrical to the centre of the part, the floor of which is directed towards the first bore 7 and the two side legs of which extend to the open end facing away from the first bore 7. An outer thread 11 is provided at the open end of the legs of the U-shaped recess 6. The outer thread 11 in the present embodiment is constructed as a left-hand thread.

In the cylindrical section 17 a pressure element 18 is accommodated, which is constructed in such a way that it has a spherical indentation 19 on its side facing the head 3, the radius of which is substantially equal to the radius of the section of the head 3 shaped like the segment of a sphere. The outer diameter of the pressure element 18 is chosen in such a way that the pressure element 18 can carry out a sliding movement in the cylindrical section 17, i.e. can be displaced in the cylindrical section 17 towards the head 3. The pressure element 18 preferably has a coaxial bore 20 which enables access to the recess 4 and also easier access to the pressure element 18.

A fixing screw 13 is further provided, which has an outer thread, i.e. a right-hand thread, which matches the inner thread 10.

Furthermore, a lock nut 14 is provided, with an inner thread which matches the outer thread 11, i.e. a left-hand thread.

In operation the screw element 1 is fed into the first bore 7 from the open end of the second bore 8. With an appropriate tool, such as, for example, a box spanner the screw element 2 can subsequently be screwed into the bone. Then the pressure element 18 and the rod 16 are inserted in succession. The screw element 1 and the receiver part 5 in this state are still fully swivellable with respect to one another. After this the fixing screw 13 is screwed into the inner thread 10 of the receiver part 5. The fixing screw 13 therein presses against the rod 16, which in turn presses against the pressure element 18, which finally presses the head 3 against the bore 7. In this way the screw element 1 and the receiver part 5 are fixed both to one another and to the rod 16.

At the same time or afterwards the lock nut 14 is screwed on to the outer thread 11 of the receiver part 5 in the screwing direction opposite the screwing direction of the fixing screw 13. The lock nut 14 and the fixing screw 13 are rotated separately from one another until each of the two parts exerts the desired holding force on the rod 16.

Owing to the thread running in the opposite direction, during tightening of the fixing screw 13 and the lock nut 14 the directions of rotation of the screw connections run in opposite directions. The substantial advantage is that the person performing the operation can apply a stronger torque on both screw connections during tightening, without a torque being introduced into the bone or, by respective countering of one tool during tightening of the screw connection, the screws being loosened again with the other tool. The stability of the screw connections is in fact ensured or even strengthened by the mutual support of the counter-torques in the tightening direction of the respective screw connection.

SECOND EMBODIMENT

A second embodiment according to FIG. 3 is described below. Corresponding parts are provided in each case with the same reference numeral and the description of them in the first embodiment should be referred to.

The screw element 1 and the receiver part 5 correspond to the first embodiment. Varying from the above-described embodiment, a head-fixing screw 12 and a rod-fixing screw 13' are provided. The head-fixing screw 12 is provided between the inner diameter 10 of the receiver part 5 and the outer diameter of the rod-fixing screw 13'. The rod-fixing screw 13' has a smaller outer diameter than the fixing screw 13 of the first embodiment.

The head-fixing screw 12 has an outer thread which matches the inner thread 10 of the receiver part. In the present embodiment this is a right-hand thread. Further, the head-fixing screw 12 is provided with a coaxial bore which has an inner thread 15 which matches the outer thread of the rod-fixing screw 13'. In the present embodiment this is a left-hand thread.

By contrast with the first embodiment the pressure element 18' is constructed as an elongated cylindrical element, extending from head 3 to beyond the rod 16 to the lower side of the head-fixing screw 12. The pressure element 18' has a U-shaped recess 18c', open towards the second end 8 and extending parallel to the U-shaped recess 6 of the receiver part 5, to receive the rod 16. The floor is constructed as cylindrical, so the rod 16 can be received. The depth of the U-shaped recess of the pressure element 18', seen in the direction of the cylindrical axis of the receiver part 5, is larger than the diameter of the rod 16 to be received, so the pressure element 18' with lateral legs 18a' and 18b' projects upwards above the rod 16. A coaxial bore, the diameter of which is smaller than the diameter of the rod 16 to be received, can adjoin the floor of the U-shaped recess.

In operation first, as in the first embodiment, the screw element 1, inserted through the second bore 8 into bore 7, with the already integrated pressure element 18', is pressed by screwing in the head-fixing screw 12 on to the head 3 in such a way that it experiences temporary rotation stabilisation. Then the rod 16 is placed into the U-shaped recesses of the receiver part and the pressure element. Subsequently the rod-fixing screw 13' is screwed into the head-fixing screw 12 and presses against the rod 16 into the floor of the recess of the pressure element 18' and fixes the rod 16.

Finally, simultaneously both the rod-fixing screw 12 can be tightened in a clockwise direction and the head-fixing screw 13' in a counter-clockwise direction with the desired holding force.

Both embodiments have in common that in the screw elements in each case slits, bores, etc. are provided which allow rotation with a rotary tool. Advantageously the two screws are tightened simultaneously, as then the advantages of the torques in opposite directions come into effect.

With this embodiment the directions of rotation of the screw connections during tightening of the rod-fixing screw 13' and the head-fixing screw 12 run in opposite directions. The substantial advantage is that the person performing the operation can apply a stronger torque on both screw connections during tightening without a torque being introduced into the bone or, by respective countering of one tool during tightening of the screw connection, the screw connections being loosened again by the other tool. The stability of the screw connections is in fact ensured or even strengthened by the mutual support of the counter-torques in the respective tightening direction of the respective screw connection.

Otherwise, the respective directions of rotation of the threads can of course be provided in reverse, i.e. that which was configured in the above embodiments as a right-hand thread can be configured as a left-hand thread and what was configured in the above configurations as a left-hand thread can be configured as a right-hand thread.

First Embodiment of a Tool

A tool, hereinafter designated as a fastening tool, is described below, which is suitable for tightening the two screw connections of the two previously described embodiments simultaneously.

FIGS. 4 and 5 show a first embodiment of a fastening tool 21. The fastening tool 21 has a first handle 22, from which extends a first shank 23. The first shank is connected as fixed against rotation to the first handle 22. At the end of the shank 23 a first screw or engagement element 27 is provided. The first shank 23 is surrounded by a second, hollow shank 24. One end of the second, hollow shank 24, facing the first handle 22, is constructed as second handle 25. At the other end of the second, hollow shank 24 a second screw or engagement element 26 is provided. The second screw or engagement element 26 surrounds the first screw or engagement element 27 concentrically. The first shank 23 and the second, hollow shank 24 can be rotated with respect to one another (arrow A and B in FIG. 4).

Mode of Operation

In order to fix a bone screw, for example of the second embodiment, a first and second screw or engagement element 26, 27 is brought into engagement with the head-fixing screw 12 and the rod-fixing screw 13'. One hand therein grips the first handle 22, while the other hand grips the second handle 25. By rotating the two handles in opposite directions of rotation the first and second screw or engagement elements 26, 27 are also twisted and tightened in opposite directions. It is also possible to perform the rotational movements of the first or the second handle 22, 25 differently or, for example, to rotate only one handle and merely to fix the other handle. That means the rotational movements can be varied depending on the torque requirement. As the torques act in opposite directions of rotation, no torque is introduced into the bone screw, ruling out endangering the patient. The torques running in opposite directions in fact mutually cancel one another out, so no torque acts on the screw element 1. A further advantage is that by means of the concentric arrangement of the first and second screw or engagement elements 26, 27 only a small space is needed, which is of great advantage during an operation, as the operating field is always only limited.

Second Embodiment of a Fastening Tool

A fastening tool according to a second embodiment is described below. Corresponding parts are provided in each case with the same reference numerals and description of them in the previous embodiment should be referred to.

FIGS. 6 to 8 show a second embodiment of a fastening tool 21'. As in the first embodiment, the fastening tool 21' has a first handle 22, from which a first, central shank 23 extends. The central shank is connected as fixed against rotation to the first handle 22. At the end of the central shank 23 a first screw or engagement element 27 is provided.

By contrast with the first embodiment, the first shank consists of a first shank section 23a and a second shank section 23b.

Gears are arranged between the first shank section 23a and the second shank section 23b. The gears are illustrated in section in FIGS. 7 and 8. Hereinafter reference is made to the enlarged illustration in FIG. 8. The gears consist of a gear housing 30, composed of a first cover 32, a substantially cylindrical sleeve component 33 and a second cover 35. The first and the second cover 32, 35 are in each case screwed to the sleeve component 33 via countersunk screws, not shown. The first cover 33 (sic) has a central bore 32a, through which the first shank section 23a projects into the inside of the gear housing. Aligned opposite, in the second cover 35 a bore 35a is also provided, through which the second shank section 23b projects into the inside of the gear housing. At the ends of the first and second shank sections 23a, 23b, located in the inside of the gear housing 30, toothed wheels 37, 38 are arranged as fixed against rotation. Fastening of the two toothed wheels takes place in each case via pins 39, 40, which extend cross-wise to the first shank through a bore, which goes through both the first and second toothed wheel and through the first and second shank sections. In this way the toothed wheels are connected as fixed against rotation to the respective shank sections. In the present embodiment the toothed wheels are constructed as bevel wheels.

In the sleeve component 33 two coaxial bores opposite one another are arranged cross-wise to the direction of the axis of the first and second shank 23, 24, through which bores a shaft 34 is pushed. Two toothed wheels 41, 42 are held as rotatable on the shaft 34. In this embodiment the toothed wheels are bevel wheels. The bevel wheels 41, 42 roll with both the toothed wheel 37 of the first shank section 23a and with the toothed wheel 38 of the second shank section 23b.

The first shank section 23a therein acts as input shaft and the second shank section 23b can act as output shaft. A torque introduced by the first shank section 23a is transferred via the toothed wheels 41, 42 to the toothed wheel 38 of the second shank section 23b. The direction of rotation is therein reversed, so the second shank section 23b rotates in a direction opposite the first shank section 23a.

Furthermore, the second, hollow shank 24 is connected as fixed against rotation to the cover 35 of the gear housing via at least one pin 36, in the present case via two pins. In this way during rotation of the gear housing the second, sleeve-shaped shank 24 is also rotated. By means of the coupling of the sleeve-shaped shank 24 to the gear housing and by means of the coupling of the two toothed wheels 41, 42 to the gear housing via the shaft 34, if the second shank section 23b is fixed a rotation of the first shank section 23a can be transferred to the sleeve-shaped shank 24 via the gear housing 30.

As in the first embodiment, a first screw or engagement element 27 is provided at the end of the second shank section 23b of the first shank 23. In the same way the first shank 23 is surrounded by the sleeve-shaped shank 24. The gear housing here forms a second handle 25 on the end of the sleeve-shaped shank 24 facing the first handle. At the other end of the sleeve-shaped shank 24 a second screw or engagement element 26 is provided. The second screw or engagement element 26 surrounds the first screw or engagement element 27 concentrically. The central shank 23 and the sleeve-shaped shank 24 can be rotated with respect to one another.

Mode of Operation

In order, for example, to fix a bone screw of the second embodiment, the first and the second screw or engagement element 26, 27 is brought into engagement with the head-fixing screw 12 and the rod-fixing screw 13'. One hand therein grips the first handle 22, while the other hand grips the gear housing 30, which serves as second handle. By rotating the two handles in opposite directions of rotation the first and second screw or engagement elements 26, 27 are also rotated and tightened in opposite directions. It is also possible to perform the rotational movements of the first or second handle or gear housing 22, 30 differently or for example to rotate only one handle and merely to fix the other handle or the gear housing. That means the rotational movements can be varied depending on the torque requirement. As the torques act in opposite directions of rotation, no torque is introduced into the screw element 1 of the bone screw, ruling out endangering the patient. Even if the gear housing 30 is held merely as fixed and a torque is introduced into the fastening tool only via the first handle 22, the torque is transferred to both the second shank section 23b of the central shank 23 and to the second, sleeve-shaped shank 24 via the gear housing 30, wherein the torques have different directions.

As in the first embodiment, a further advantage is that owing to the concentric arrangement of the first and second screw or engagement elements 26, 27 only a small space is needed, which is of great advantage in an operation, as the operating field is always only limited.

The bone screw is not restricted to the embodiment as polyaxial screw described here. The bone screw can in fact also be constructed as a monoaxial screw, according to which the screw head 3 and the receiver part 5 are constructed in one piece.

What is claimed is:

1. A bone screw comprising:
   a screw element comprising a screw shank and a screw head;
   a cylindrical receiver part for receiving a rod to be connected to the bone screw,
   the receiver part having a first end, a cylindrical axis, a bore coaxial to the cylindrical axis coming from the first end, an opening extending cross-wise to the cylindrical axis for receiving the rod, and a first inner thread at the first end;
   a first screw cooperating with the first inner thread, the first screw having a central bore and a second an inner thread; and
   a second screw cooperating with the second inner thread for fixing the rod in the cylindrical receiving part;
   wherein the first inner thread and the second an inner thread are structured and arranged to run in apposite directions.

2. The bone screw according to claim 1, wherein the opening comprises a U-shaped recess open to the first end.

3. The bone screw according to claim 1, further comprising a pressure element in the receiver part for contact with the screw head.

4. The bone screw according to claim 3, wherein the pressure element and the first screw are one piece.

5. The bone screw according to claim 4, wherein the pressure element comprises a recess for receiving the rod, the recess having a depth in the axial direction which is greater than a diameter of the rod.

6. A bone screw according to claim 1, wherein the cylindrical receiver part comprises an outer surface, the bone screw further comprising a snap ring provided on the outer surface at the first end.

7. A bone screw according to claim 1, wherein the second screw exerts pressure on the rod and fixes the rod.

* * * * *